US011197886B2

(12) United States Patent
Pilotto et al.

(10) Patent No.: US 11,197,886 B2
(45) Date of Patent: Dec. 14, 2021

(54) PHARMACEUTICAL COMPOSITIONS WITH HYDRATING AND LUBRICATING ACTIVITY

(71) Applicant: FIDIA FARMACEUTICI S.P.A., Abano Terme (IT)

(72) Inventors: Laura Pilotto, Abano Terme (IT); Giovanni Gennari, Abano Terme (IT); Anna Maria Zanellato, Abano Terme (IT)

(73) Assignee: FIDIA FARMACEUTICI S.p.A., Abano Terme (IT)

( * ) Notice: Subject to any disclaimer, the term of this patent is extended or adjusted under 35 U.S.C. 154(b) by 0 days.

(21) Appl. No.: 16/593,616

(22) Filed: Oct. 4, 2019

(65) Prior Publication Data

US 2020/0030365 A1   Jan. 30, 2020

Related U.S. Application Data

(63) Continuation of application No. 15/038,924, filed as application No. PCT/EP2014/074736 on Nov. 17, 2014, now abandoned.

(30) Foreign Application Priority Data

Nov. 26, 2013   (IT) .......................... MI2013A001971

(51) Int. Cl.
| | | |
|---|---|---|
| *A61K 31/728* | (2006.01) | |
| *A61K 9/00* | (2006.01) | |
| *A61K 9/06* | (2006.01) | |
| *A61K 9/02* | (2006.01) | |
| *A61K 9/12* | (2006.01) | |
| *A61K 9/08* | (2006.01) | |
| *A61K 47/36* | (2006.01) | |

(52) U.S. Cl.
CPC .......... *A61K 31/728* (2013.01); *A61K 9/0034* (2013.01); *A61K 9/02* (2013.01); *A61K 9/06* (2013.01); *A61K 9/08* (2013.01); *A61K 9/122* (2013.01); *A61K 47/36* (2013.01)

(58) Field of Classification Search
CPC ...... A61K 31/728; A61K 9/0034; A61K 9/06; A61K 9/02; A61K 9/122
USPC .......................................................... 514/54
See application file for complete search history.

(56) References Cited

U.S. PATENT DOCUMENTS

| | | |
|---|---|---|
| 6,824,793 B1 | 11/2004 | O'Hagan et al. |
| 2003/0181689 A1* | 9/2003 | Bellini ................... A61L 27/20 536/2 |
| 2004/0192642 A1 | 9/2004 | Yang et al. |
| 2005/0095219 A1 | 5/2005 | Yang et al. |
| 2005/0181057 A1 | 8/2005 | Rosenberg et al. |
| 2009/0186105 A1 | 7/2009 | Reiner et al. |
| 2010/0249156 A1 | 9/2010 | Caramelia et al. |

FOREIGN PATENT DOCUMENTS

WO   WO-2006089561 A1 *   8/2006

OTHER PUBLICATIONS

Fidia Farmaceutici S.p.A.; Nov. 2009.*
Food and Drug Administration; May 7, 2010.*
Acarturk (Recent Patents on Drug Delivery & Formulation, vol. 3, No. 3. Nov. 2009, pp. 193-205(13)) (abstract sent).
Baloglu et al. (J Pharm Pharmaceut Sci (www.cspsCanada.org) 12(3) 312- 336, 2009).
Chen et al. (The Journal of Sexual Medicine; vol. 10, issue 6, Jun. 2013, pp. 1575-1584).
Chen et al., "Evaluation of the Efficacy and Safety of Hyaluronic Acid Vaginal Gel to Ease Vaginal Dryness: A Multicenter, Randomized, Controlled, Open-Label, Parallel-Group, Clinical Trial", The Journal of Sexual Medicine, vol. 10, No. 6, Jun. 2013, pp. 1575-1584.
International Search Report (PCT/ISA/210) issued PCT/EP2014/074736, dated Feb. 6, 2015.
Karaosmanoglu et al., "Hyaluronic acid in the treatment of postmenopausal women with atrophic vaginitis", International Journal of Gynecology and Obstetrics, vol. 113, No. 2, May 2011, pp. 156-157.
Lee et al. (Journal of the European Academy of Dermatology and Venereology, May 2008; 22(5): 590-595) (abstract sent).
Sanzgiri et al., "Evaluation of mucoadhesive properties of hyaluronic acid benzyl esters", International Journal of Pharmaceutics, vol. 107, 1994, pp. 91-97.
Written Opinion (PCT/ISA/237) issued PCT/EP2014/074736,dated Feb. 6, 2015.

* cited by examiner

*Primary Examiner* — Shaojiaa Jiang
*Assistant Examiner* — Michael C Henry
(74) *Attorney, Agent, or Firm* — Birch, Stewart, Kolasch & Birch, LLP

(57) ABSTRACT

The present invention discloses pharmaceutical compositions comprising ester derivatives of hyaluronic acid for use as a topical treatment in disorders of the vaginal mucosa characterised by loss of elasticity and hydration, such as vaginal dryness and/or atrophic vaginitis; said compositions can also be used successfully to lubricate the genital mucosa.

2 Claims, No Drawings

PHARMACEUTICAL COMPOSITIONS WITH HYDRATING AND LUBRICATING ACTIVITY

CROSS REFERENCE TO RELATED APPLICATIONS

This application is a Continuation of copending application Ser. No. 15/038,924, filed on May 24, 2016, which is the National Phase under 35 U.S.C. § 371 of International Application No. PCT/EP2014/074736, filed on Nov. 17, 2014, which claims the benefit under 35 U.S.C. § 119(a) to Patent Application No. MI2013A001971, filed in Italy on Nov. 26, 2013, all of which are hereby expressly incorporated by reference into the present application.

FIELD OF THE INVENTION

The present invention discloses pharmaceutical compositions comprising ester derivatives of hyaluronic acid for use as a topical treatment in disorders of the vaginal mucosa characterised by loss of elasticity and hydration, such as vaginal dryness and/or atrophic vaginitis, and as lubricants for the genital mucosa.

BACKGROUND OF THE INVENTION

The vaginal mucosa is the surface of the vagina facing the lumen. It consists of a thick multi-layered lining epithelium without keratin but protected by mucus, which is rich in mucopolysaccharides secreted by muciparous cells. The cells of the vaginal mucosa, especially those of the outermost layers, are hormone-correlated, and play an important part in maintaining the metabolic balance of the vaginal environment. Said cells are therefore stimulated by oestrogens to synthesise and store large quantities of glycogen (sugar reserve), which is introduced into the vaginal lumen when said cells are shed. The glycogen released is metabolised by the bacterial flora normally present in the vagina, with the formation of lactic acid responsible for the acid local pH, especially towards the middle of the menstrual cycle. Lactobacilli form a biofilm that coats the vaginal mucosa and, together with the low pH, protects the environment against aggression by pathogenic and opportunistic micro-organisms and against excessive growth of bacteria which are innocuous in themselves, and normally present in small amounts in the vagina as normal "resident" microbial flora.

The innermost layer of the mucosa, the lamina propria, consists of fibroelastic connective tissue, and its deepest parts are richly vascularised. Although the vaginal mucosa does not contain glands, stimulation, arousal and sexual intercourse increase the secretion, which serves to lubricate its surface. This secretion actually originates from the glands of the cervix, together with the transudate originating from the lamina propria.

It will easily be deduced from this complex picture that any variation in the vaginal equilibrium leads to alterations of the mucosa, which tends to lose its hydration and turgidity, giving rise to vaginal dryness. The hydration and lubrication, thickness, structure and functionality of the vulvovaginal mucosa change from birth to menopause, throughout the woman's fertile life, but the major changes take place during and after the menopause, when oestrogen stimulation is drastically reduced. Other causes of vaginal dryness are the post-partum period, lactation, chronic use of some drugs (such as antitumorals, antidepressants and antihistamines), surgical operations (removal of the ovaries) and concomitant disorders such as obesity or diabetes. There are also mental and physical causes such as stress, particularly restrictive diets, intense physical activity, and serious social problems.

Finally, dryness can be caused by mental or relationship problems that prevent regular mucus production during the stages of sexual arousal.

Vaginal dryness, regardless of cause, affects about 50% of women, and is manifested by a sensation of dryness, vaginal itching, discomfort, pain during sexual intercourse and, in the more obstinate forms, inflammation and urinary problems. The altered trophism of the vaginal mucosa paves the way for opportunistic fungal or bacterial infections; in these situations, the disorder is more specifically called vaginal atrophy or atrophic vaginitis.

The treatment of vaginal dryness and atrophic vaginitis, apart from pharmacological treatment of the bacterial or fungal infection or hormone replacement treatment (which is not always applicable), is mainly comprising the use of lubricants with a soothing and emollient action, characterised by the carrier of which they are composed. Lubricants may be:

oil-based: generally polymer gels derived from petroleum. They have a long-lasting effect, because they do not dry on contact with air and do not interact unfavourably with bodily fluids, but are not very lubricant (they produce friction) and above all dissolve latex, which means that they cannot be used with a condom, as they would reduce its contraceptive efficacy and its efficacy against sexually transmitted diseases;

silicone-based: the latest generation, which resemble hydrogels. They are easily spread and dry slowly, but can attack silicone-based products;

water-based: gels with a high water content which are easily spreadable, compatible with biological fluids and have no effect on the latex of which condoms are made; however, although they give an excellent sensation of well-being after application, they dry very easily, and consequently require frequent application.

Water-based products are certainly the most widely used when not only extempore lubrication, but also a long-lasting lubricating, emollient, protective effect, is required.

One of the ingredients most widely used in these preparations is hyaluronic acid (HA), a polymer ubiquitously present in the human body which possesses multiple properties; in particular, for topical application it acts as a hydrating, emollient, mucoadhesive, healing and tissue-regenerating agent. It absorbs a great deal of water (up to 1000 times its own weight) and gives rise to water-soluble gels which are easily spread and comfortable to apply. However, the high water content causes them to dry quite quickly.

It has now surprisingly been found that some hyaluronic acid derivatives, obtained by esterification of HA, can be used successfully in these applications, overcoming all the problems existing in the state of the art.

Some HA ester derivatives have already been successfully used in other fields, such as tissue engineering; as described in EP618817, for example, 75 or 100% derivatives can be reduced to fibres which, when processed in the form of non-woven fabrics, constitute a three-dimensional matrix usable in the dermatological field.

The pharmaceutical compositions of the invention consist of hyaluronic acid ester with benzyl alcohol, wherein 50% of the carboxyl groups of hyaluronic acid are esterified with the corresponding hydroxyl groups of benzyl alcohol (Hyaff11p50); the ester thus obtained absorbs less water than HA "as is", is less water-soluble and more compact but, surprisingly, also performs a more effective, longer-lasting moisturising effect than known preparations containing HA sodium salt.

The compositions of the invention therefore contribute significantly to improving the trophism and hydration of vaginal mucosa subject to dryness.

DETAILED DESCRIPTION OF THE INVENTION

The present invention discloses pharmaceutical compositions comprising hyaluronic acid benzyl ester, wherein 50% of the carboxyl groups of hyaluronic acid are esterified with the corresponding hydroxyl groups of benzyl alcohol (hyaluronic acid 50% esterified with benzyl alcohol; Hyaff11p50), for use as a topical treatment of disorders of the vaginal mucosa characterised by loss of elasticity and hydration, such as vaginal dryness and atrophic vaginitis, possibly accompanied by concomitant inflammations or bacterial or fungal infections; said compositions can also be used successfully as lubricants of the genital mucosa, even under physiological conditions.

The starting hyaluronic acid used in the present invention can derive from any source, such as extraction from rooster combs (EP138572), from fermentation, as known, or from biosynthesis (from *Bacillus*, WO2012032154), and have an average molecular weight ranging between 100,000 and 250,000 Da, in particular between 180,000 and 230,000 Da. It should be noted that average molecular weight here means weight-average molecular weight, calculated by the "intrinsic viscosity" method (Terbojevich et al., *Carbohydr Res*, 1986, 363-377).

The ester derivative used herein is obtained as described in EP216453, and specifically as detailed in Example 1:

Example 1: Preparation of Hyaluronic Acid Benzyl Ester Wherein 50% of the HA Carboxyl Groups are Esterified with Benzyl Alcohol (Hyaff1p50)

10.6 g of HA tetrabutylammonium salt (weight-average molecular weight 200,000 Da), corresponding to 17 milliequivalents of monomer units, is solubilised in 530 ml of dimethyl sulphoxide at 25° C., 7.8 milliequivalents of benzyl bromide are added, and the resulting solution is maintained at 30° C. for 12 hours. A solution of 62 ml of water containing 9 g of sodium chloride is then added, and the resulting mixture is poured slowly into 3000 ml of acetone under constant stirring. The precipitate that forms is filtered, washed three times with 500 ml of acetone/water 5:1, and finally dried under vacuum at 30° C. for eight hours. The precipitation stage is repeated; the precipitate is washed twice with acetone/water 5:1 and then three times with acetone alone, followed by drying under vacuum at 30° C. for 24 hours.

The end product thus obtained is hyaluronic acid wherein 50% of its carboxyl groups are esterified with the corresponding hydroxyls of benzyl alcohol (Hyaff11p50). The quantitation of the ester groups is performed according to Cundiff and Markunas, *Anal Chem*, 1961, 33, 1028-1030.

The ester derivative thus obtained absorbs water to a lesser extent than the starting molecule. The replacement of 50% of the carboxyls with the aromatic groups of benzyl alcohol reduces the hydrophilicity of the starting molecule for obvious chemical reasons and also for steric reasons; however, as described below, Hyaff11p50 unexpectedly proved to be:

far superior to HA "as is" in hydrating the mucosa, maintaining a long-lasting effect of freshness and well-being, though containing a lower percentage of water;
able to exercise a bacteriostatic action which is useful in the event of opportunistic infections;
longer-lasting, due to its lower solubility in water;
harmless to latex, because it has a completely aqueous base, and can therefore be used with condoms;
mucoadhesive and biocompatible;
and therefore represents a definite improvement on the range of vaginal hydrating and lubricating products currently available. It can be used for the purposes described herein in concentrations ranging between 0.1 and 1%, preferably between 0.2 and 5%, and most preferably at the concentration of 0.2% (w/w).

Example 2: Evaluation of the Hydrating Effect of a Preparation of HA (Formulation A) and a Preparation of Hyaff11p50 (Formulation B) Wherein the Average MW of HA is 180,000-230,000 Da The formulations were prepared simply by hydrating HA powders "as is" or Hyaff11p50 with an isotonic saline solution (NaCl 0.9% w/v in water) to obtain a final concentration of 0.2%.

The study was conducted ex-vivo on porcine vaginal mucosa obtained by surgical removal and devoid of pathological diseases.

Samples of vaginal mucosa with an area of 2 $cm^2$ were placed on Petri dishes and treated with 1 ml of Formulation A or Formulation B, or with an equal volume of saline solution (Control).

The samples were then moistened with 1 ml of saline solution to simulate the vaginal environment, and stored in an incubator at 37° C. with constant humidity. After one hour, the strips of mucosa were transferred to dry Petri dishes and, taking this as Time 0 and the maximum level of hydration, their degree of hydration was evaluated, the control value having being set at 100. The degree of hydration of the mucosa was measured at pre-set times (1, 3, 6 and 24 hours, corresponding to T1, T2, T3 and T4), the samples being kept in the incubator between one measurement and the next. The measurement was conducted with a corneometer; the dielectric power of the water contained in the surface, which obviously varies with the water content, is measured by applying a sensor to the test surface.

The results obtained, which are set out in Table 1 below, unequivocally demonstrate that Formulation B (Hyaff11p50) has a much better moisturising effect than Formulation A (HA); after 24 hours the residual hydration level of the samples treated with Hyaff11p50 was more than twice that of the samples treated with HA. This means that Formulation B yields more water to the mucosa than Formulation A.

TABLE 1

Evaluation of degree of hydration of porcine vaginal mucosa samples

| Product | T1 | T2 | T3 | T4 |
|---|---|---|---|---|
| Control | 41.5 | 28.3 | 13.4 | 2.2 |
| Formulation A (HA) | 54.7 | 37.6 | 19.7 | 5.3 |
| Formulation B (Hyaff11p50) | 93.5 | 71.7 | 30.1 | 11.5 |

This result is surprising, and above all entirely unexpected, as HA absorbs far more water than the Hyaff11p50 tested.

In addition to its proven hydrating properties, the Hyaff11p50 used here also exercises a mild but important bacteriostatic effect due to the benzyl alcohol released by the molecules by simple hydrolysis in an aqueous environment, in the absence of specific enzymes (according to Example 3). As already stated, vaginal dryness and atrophy are often accompanied by opportunistic infections; a product that keeps this aspect under control, thereby eliminating the need for specific pharmacological treatments, would therefore be very useful. These treatments are usually administered locally, and therefore have an adverse effect on an already fragile mucosa. The release of benzyl alcohol from the products claimed herein can, however, inhibit the proliferation of opportunistic pathogens, as benzyl alcohol possesses bacteriostatic properties (Merck Index, 14th Edition, § 1124), but without adversely interacting with the cells of the vaginal mucosa.

Example 3: Evaluation of Release of Benzyl Alcohol from Hyaff11p50 in an Aqueous Environment Hyaff11p50 was dissolved in water and incubated in isotonic saline solution (NaCl 0.9% w/v in water) at the concentration of 1 mg/ml at 37° for 3 days. The presence of benzyl alcohol in the incubation medium was detected by HPLC using a C18 column and a UV detector, and measured after 24, 48 and 72 hours (T1, T2 and T3 respectively). The results, calculated as the percentage of benzyl alcohol compared with the initial content, are set out in Table 2 below. The release of benzyl alcohol, in the total absence of enzymes, is clearly substantial, consistent and linear.

TABLE 2

| Evaluation of release of benzyl alcohol into the medium | | | |
|---|---|---|---|
| | T1 | T2 | T3 |
| Benzyl alcohol in medium (% of initial content) | 34% | 57% | 79% |

This means that after application to the vaginal mucosa, the benzyl alcohol released can combat any bacteria and fungi present, which find a fertile medium in vaginal mucosa altered by dryness.

In view of this discovery, the Applicant has devised some pharmaceutical compositions comprising Hyaff11p50 which are suitable for intravaginal application or other application to the genital apparatus, even free from the classic preservatives (parabens), which are often a source of discomfort and stinging when applied to an inflamed mucosa, or of local allergies in particularly sensitive individuals. The Applicant has surprisingly discovered that replacing parabens with precise glycol excipients does not alter the hydrating and lubricating characteristics of the product, or modify its storability.

As stated, the pharmaceutical compositions according to the invention can be prepared in the classic pharmaceutical forms suitable for vaginal use, namely ovules, douches and products applied by spreading (creams or gels).

The vaginal ovules on the market are generally formulated in oily carriers which may be unsatisfactory in many respects; for example, the ovule tends to slip as the oily excipients are dissolved by body heat, thus creating significant discomfort. In the case of the invention, due to the special characteristics of Hyaff11p50, the ovules can be formulated with hydrophilic excipients and gelled with gelatin. In this way, as the hyaluronic acid derivative is mucoadhesive, the ovule adheres perfectly to the vaginal mucosa after insertion, and remains in situ for a considerable time without causing discomfort. To facilitate its application to very dry, atrophic mucous membranes, polymers that increase the mucoadhesion of the end product can be included in the formulation of the ovules. Some examples are derivatives of acrylic acid, cellulose (hydroxyethylcellulose, carboxymethylcellulose) or other polymers known.

During its residence in the vaginal channel the hydrogel-like mass of ovule gradually releases water, and exercises over time its hydrating, lubricant and refreshing action and also its antibacterial action, due to benzyl alcohol which, as demonstrated, is released by hydrolysis into the aqueous environment. The ovules described herein are particularly useful in the continuous treatment of vaginal dryness or atrophy accompanied by minor bacterial infections or opportunistic mycosis.

On the other hand, vaginal douches are more useful as an extemporary hydrating, refreshing, soothing and optionally cleansing treatment, to be used alone or together with other local pharmacological treatments.

Among the pharmaceutical forms which can be applied by direct spreading, the preferred form is the gel, wherein the solution of Hyaff11p50 is gelled with acrylic acid polymers belonging to the carbomer family; of the various carbomers, Carbomer 974P (Carbopol®974P, Lubrizol®) will preferably be selected, as it possesses mucoadhesive properties that are particularly useful in this type of formulation.

Other forms suitable for vaginal administration include foams or mousses formulated with or without propellants such hydrofluorocarbons, butane or other inert gases.

The compositions are described herein purely for demonstration purposes, the choice of the most suitable excipients being left to the skilled person.

Example 4: Preparation of a Pharmaceutical Composition in the Form of a Gel Comprising 0.2% Hyaff11p50 (% w/w)

| | |
|---|---|
| Hyaff11p50 | 0.2 |
| Propylene glycol | 10 |
| Methyl parahydroxybenzoate | 0.2 |
| Propyl parahydroxybenzoate | 0.03 |
| Carbopol ®974P | 1 |
| NaOH | q.s. for pH 5.5-6.5 |
| Purified water | q.s. for 100 |

Methyl parahydroxybenzoate and propyl parahydroxybenzoate are dissolved, under stirring, in about 98% of the total water, heated to 80° C. The solution is slowly cooled to 35-40° and Hyaff11p50 added, mixing for about 30 minutes. When dissolution is complete, the propylene glycol is added, followed by Carbopol 974P, under vacuum. NaOH is dissolved in the remaining quantity of water and added to the homogenous gel obtained in the previous steps, adjusting the pH to values ranging between 5.5 and 6.5.

Example 5: Preparation of a Pharmaceutical Composition in Gel Form Comprising 0.2% Hyaff11p50 without Paraben Preservatives (% w/w)

| | |
|---|---|
| Hyaff11p50 | 0.2 |
| Propylene glycol | 5.767 |
| MP-Diol ® glycol | 3.750 |
| Symdiol 68 | 0.9 |
| Carbopol ®974P | 1 |
| NaOH | q.s. for pH 5.5-6.5 |
| Purified water | q.s. for 100 |

Hyaff11p50 is added under stirring to about 98% of the total water, heated to 40° C., and mixed until dissolved. Propylene glycol and MPDiol® Glycol are then added under stirring, and mixed until dissolved. Carbopol 974P is dispersed under stirring, avoiding the formation of lumps.

NaOH is solubilised separately in the remaining quantity of water; said solution is then added to the preceding one under stirring, and stirring continues for 10 minutes, until a homogenous gel is obtained; the gel is then cooled to ambient temperature, mixing slowly. Finally, Symdiol 68 is added under stirring and mixed until the gel is homogeneous.

Example 6: Preparation of a Pharmaceutical Composition in the Form of Vaginal Ovules Comprising Hyaff11p50 0.2% without the Addition of Mucoadhesive Polymers (% w/w)

| | |
|---|---|
| Hyaff11p50 | 0.2 |
| Glycerol 98% Ph. Eur. | 48.35 |
| MP-Diol ® glycol | 3.750 |
| Symdiol 68 | 0.9 |
| 220 bloom gelatin | 13.50 |
| Lactic acid | q.s. for pH 4.7-5.00 |
| Purified water | q.s. for 100 |

88% of the purified water is heated to 70° C., and gelatin is added slowly under stirring. Stirring continues until complete dissolution, thereby obtaining a clear, homogeneous phase, that is left under gentle stirring and heating to promote deaeration of the phase.

Glycerol, MP-Diol® Glycol and Symdiol 68 are mixed until a clear, homogeneous phase is obtained. Hyaff11p50 is added under stirring, and left under stirring until complete dispersion. The remainder of the purified water is added under stirring. The mixture is heated to 70-72° C., always under stirring, until a clear homogeneous phase forms.

The two phases previously obtained are combined under stirring at 70° C., and left under stirring for at least 30 minutes.

Lactic acid is added under stirring to adjust the pH to values ranging between 4.70 and 5.00.

The mixture is cooled to 50+/−5° C. and poured into moulds to obtain ovules weighing 2200 mg each.

Example 7: Preparation of a Pharmaceutical Composition in the Form of Vaginal Ovules Comprising Hyaff11p50 0.2% with the Addition of Mucoadhesive Polymer (Carbopol® 974P) (% w/w)

| | |
|---|---|
| Hyaff11p50 | 0.2 |
| Glycerol 98% Ph. Eur. | 48.35 |
| MP-Diol ® glycol | 3.750 |
| Symdiol 68 | 0.9 |
| 220 bloom gelatin | 13.50 |
| Lactic acid | q.s. for pH 4.7-5.00 |
| Carbopol ® 974P | 0.1 |
| Purified water | q.s. for 100 |

Preparation: 88% of the purified water is heated to 70° C., and gelatin is added slowly under stirring. Stirring continues until complete dissolution, thereby obtaining a clear, homogeneous phase that is left under gentle stirring and heating to promote deaeration of the phase.

Glycerol, MP-Diol® Glycol and Symdiol 68 are mixed until a clear, homogeneous phase is obtained. Carbopol® 974P is added under stirring, and left under stirring until complete dispersion. Hyaff11p50 is added under stirring, and left under stirring until complete dispersion. The remainder of the purified water is added under stirring. The mixture is heated to 70-72° C., always under stirring, until a clear homogeneous phase forms.

The two phases previously obtained are combined under stirring at 70° C., and left under stirring for at least 30 minutes.

Lactic acid is added under stirring to adjust the pH to values ranging between 4.70 and 5.00.

The mixture is cooled to 50+/−5° C. and poured into moulds to obtain ovules weighing 2200 mg each.

Example 8: Preparation of a Pharmaceutical Composition in the Form of Vaginal Ovules Comprising Hyaff11p50 0.2% with the Addition of Mucoadhesive Polymer (Hydroxyethylcellulose) (% w/w)

| | |
|---|---|
| Hyaff11p50 | 0.2 |
| Glycerol 98% Ph. Eur. | 48.35 |
| MP-Diol ® glycol | 3.750 |
| Symdiol 68 | 0.9 |
| 220 bloom gelatin | 13.50 |
| Lactic acid | q.s. for pH 4.7-5.00 |
| Hydroxyethylcellulose (Natrosol HHX) | 0.2 |
| Purified water | q.s. for 100 |

Preparation: see Example 7

Example 9: Preparation of a Pharmaceutical Composition in the Form of Vaginal Ovules Comprising Hyaff11p50 0.2% with the Addition of Mucoadhesive Polymer (Sodium Carboxymethylcellulose) (% w/w)

| | |
|---|---|
| Hyaff11p50 | 0.2 |
| Glycerol 98% Ph. Eur. | 48.35 |
| MP-Diol ® glycol | 3.750 |
| Symdiol 68 | 0.9 |
| 220 bloom gelatin | 13.50 |
| Lactic acid | q.s. for pH 4.7-5.00 |

-continued

| | |
|---|---|
| Sodium carboxymethylcellulose (Blanose 7MF) | 0.2 |
| Purified water | q.s. for 100 |

Preparation: see Example 8

Example 10: Preparation of a Pharmaceutical Composition in the Form of a Vaginal Douche Comprising Hyaff11p50 0.2% (% w/w)

| | |
|---|---|
| Hyaff11p50 | 0.2 |
| Sodium benzoate | 0.3 |
| Potassium sorbate | 0.2 |
| Lactic acid | q.s. for pH 4.5 |
| Purified water | q.s. for 100 |

Hyaff11p50 is added to the quantity of water required by the formula, and stirred until complete dissolution. Sodium benzoate and potassium sorbate are then added, and stirred until complete dissolution. Finally, lactic acid is added under stirring until pH 4.5, and stirring continues until a homogenous solution is obtained.

Example 11: Preparation of a Pharmaceutical Composition in the Form of a Vaginal Douche Comprising Hyaff11p50 0.2% Containing a Detergent (% w/w)

| | |
|---|---|
| Hyaff11p50 | 0.2 |
| Sodium benzoate | 0.3 |
| Potassium sorbate | 0.2 |
| Lactic acid | q.s. for pH 4.5 |
| Cocamidopropyl betaine (detergent) | 0.5 |
| Purified water | q.s. for 100 |

Hyaff11p50 is added to the quantity of water required by the formula, and stirred until completely dissolved. Sodium benzoate and potassium sorbate are then added, and stirred until complete dissolution. Finally, the detergent is added, and mixing continues until complete dissolution. Finally, lactic acid is added under stirring until pH 4.5, and stirring continues until homogenous.

The invention claimed is:

1. A method of bacteriostatic treatment of bacterial infections in a subject in need thereof comprising locally administering a pharmaceutical composition in form of gel, ovules, douches, foam or mousse, comprising hyaluronic acid, wherein 50% of the hyaluronic acid carboxyl groups are esterified with benzyl alcohol
   wherein the hyaluronic acid 50% esterified with benzyl alcohol is obtained starting from a hyaluronic acid having an average molecular weight ranging between 180,000 and 230,000 Da and has a concentration of 0.2% w/w.

2. The method according to claim 1, wherein the composition is a gel comprising hyaluronic acid 50% esterified with benzyl alcohol at the concentration of 0.2% w/w, Carbomer 974P as gelling agent and pharmaceutically acceptable excipients, wherein the hyaluronic acid 50% esterified with benzyl alcohol is obtained starting from a hyaluronic acid having a weight-average molecular weight ranging between 180,000 and 230,000 Da.

* * * * *